United States Patent [19]

Cereda et al.

[11] 4,386,099

[45] May 31, 1983

[54] IMIDAZOLYLPHENYL AMIDINES, PHARMACEUTICAL COMPOSITIONS CONTAINING SAME AND USE THEREOF

[75] Inventors: Enzo Cereda, Tortona; Arturo Donetti, Milan; Piero del Soldato; Mario Bergamaschi, both of Monza, all of Italy

[73] Assignee: Istituto de Angeli S.p.A., Milan, Italy

[21] Appl. No.: 322,903

[22] Filed: Nov. 19, 1981

[30] Foreign Application Priority Data

Nov. 28, 1980 [IT] Italy ............................... 26323 A/80

[51] Int. Cl.³ ................... A61K 31/415; C07D 233/64
[52] U.S. Cl. ............................... 424/273 R; 424/272; 548/245; 548/336; 548/346
[58] Field of Search ....................... 548/336, 346, 245; 424/273 R, 272

[56] References Cited

U.S. PATENT DOCUMENTS 4,225,724 9/1980 Warner et al. ...................... 548/346

Primary Examiner—Robert W. Ramsuer
Attorney, Agent, or Firm—Hammond & Littell, Weissenberger and Muserlian

[57] ABSTRACT

This invention relates to imidazolylphenyl amidines, the preparation thereof, and pharmaceutical compositions containing them. More particularly, this invention relates to compounds of the general formula

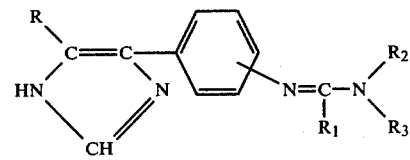

in which R, $R_1$, $R_3$, which may be the same or different, each represent a hydrogen atom or a lower alkyl group, and $R_2$ represents a linear or branched alkyl, alkenyl, or alkynyl group, a cyano group, a hydroxyl group, a substituted or unsubstituted cycloalkyl or cycloaliphatic alkyl group, a bicyclic group, an aralkyl or aryl group optionally substituted by halogen, methyl, methoxy, or methylenedioxy groups, or a substituted or unsubstituted heterocyclylalkyl or heterocyclic group which may also contain a further hetero atom, or a non-toxic, pharmacologically acceptable acid addition salt thereof. These compounds are useful in treating disorders of the gastrointestinal tract.

20 Claims, No Drawings

IMIDAZOLYLPHENYL AMIDINES, PHARMACEUTICAL COMPOSITIONS CONTAINING SAME AND USE THEREOF

FIELD OF THE INVENTION

This invention relates to novel imidazolylphenyl amidines, the preparation thereof, and pharmaceutical compositions containing them. More particularly, this invention relates to novel pharmacologically active substituted imidazolylphenyl amidines which are H$_2$-receptor blocking agents, which inhibit gastric acid secretion, and which are useful anti-ulcer agents.

BACKGROUND OF THE INVENTION

The ineffectiveness of the ordinary antihistaminic drugs in blocking the stimulating effect of histamine on gastric secretion has prompted the search for histaminic antagonists involved in this response. This effect of histamine, which is recognized as a powerful stimulator of gastric secretion, is communicated through H$_2$-receptors [Black et al., Nature 236, 385 (1972)] and is not inhibited by the classical antihistamines, H$_1$-receptor blockers [Ash and Schild, Brit. J. Pharmacol., 27, 427 (1966)]. Investigations in this direction culminated in the synthesis of a class of substances [G. J. Durant et al., J. Med. Chem. 20, 901 (1977)] typified by burimamide, the first clinically effective H$_2$-receptor antagonist. Although burimamide was sufficiently selective pharmacologically, it seemed to lack sufficient oral bioavailability. Metiamide, a subsequently evaluated H$_2$-antagonist, proved more potent and orally active in man than burimamide. However, metiamide could not be used in therapy due to its toxic side effects (agranulocytosis).

Cimetidine, a congener of metiamide bearing a cyanoguanidino group instead of a thioureido group, proved as potent as metiamide as an H$_2$-antagonist but was devoid of the toxic side effects of metiamide. Cimetidine has been recently used therapeutically as an anti-ulcer drug. Its half-life, however, is relatively short, and administration of several daily doses of 200 to 300 mg tablets is required. This shortcoming has prompted further research into the H$_2$-receptor blockers area aimed at finding longer acting and/or more potent substances. Recently, two new H$_2$-receptor antagonists—ranitidine (AH 19065) and tiotidine (ICI 125,225)—have been reported as possessing chemical features analogous to cimetidine, i.e., a linear methylthioethyl side-chain bearing neutral polar groups. The main chemical variation in the latter compounds with respect to cimetidine consists of the replacement of the imidazole by an aminoalkyl furan and a 2-guanidinothiazole ring, respectively. Both ranitidine [Bradshaw et al., Brit. J. Pharmacol. 66 464 P (1979)] and tiotidine [T. O. Yellin, Life Sci., 25, 2001–2009 (1979)] have been reported to be more potent than cimetidine either as H$_2$-receptor antagonists during in vitro testing or as inhibitors of gastric acid secretion during in vivo testing.

DETAILED DESCRIPTION OF THE INVENTION

It has now been found that by substituting the linear side-chain, present in the classical antagonists as well as in the two more recent H$_2$-receptor antagonists, with a phenyl ring having optionally substituted amidino groups, novel substances have been obtained which are endowed with potent H$_2$-receptor blocking activity and thus inhibit gastric acid secretion. The H$_2$-receptor antagonists useful in blocking gastric secretion agents are also potentially useful as therapeutically active agents in the fields of inflammation [T. Yoshioka et al., Am. J. Surg. 136, (1981)] and of cardiovascular disorders [Jerome P. Trzechiakowski et al., J. Pharmacol. Exp. Ther. 214, 629,634 (1980)]. In some instances compounds of the invention may be useful as combined H$_1$- and H$_2$-antagonists [Barry L. Tepperman et al., Life Sciences, Vol. 24, 2301–2308 (1979)], since some compounds of the present invention show both these receptorial interactions.

According to the present invention compounds of the general formula

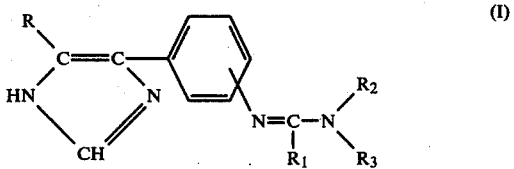

in which R, R$_1$, and R$_3$, which may be the same or different, represent a hydrogen atom or a lower alkyl group, and R$_2$ represents a linear or branched alkyl, alkenyl, or alkynyl group, a cyano group, a hydroxyl group, a substituted or unsubstituted cycloalkyl or cycloaliphatic alkyl group, a bicyclic group, an aralkyl or aryl group optionally substituted by halogen, methyl, methoxy, or methylenedioxy groups, or a substituted or unsubstituted heterocyclylalkyl or heterocyclic group which may also contain a further hetero atom, and non-toxic acid addition salts thereof.

The term "non-toxic" herein used designates salts formed with either inorganic or organic acids, the anionic portions of which salts are pharmacologically compatible in the doses at which the salts are administered. Suitable salts include those formed with, for example, hydrochloric acid, maleic acid, furmaric acid, methanesulfonic acid, citric acid, tartaric acid, or acetic acid.

It is understood that for convenience in this specification reference to the compounds of the invention or the compounds of Formula I includes the compounds themselves as bases as well as the corresponding salts. It is also understood that although in Formula I the double bond in the amidine radical and in the imidazole ring has been inserted in a particular position, various other tautomeric forms are possible, and the present invention includes such tautomeric forms within its scope, both in terms of the compounds of the inventions and in terms of the preparation procedures.

When in the compounds of Formula I R, R$_1$, and/or R$_3$ represent lower alkyl groups, these may be alkyl groups containing from 1 to 3 carbon atoms, for example, methyl. When R$_2$ represents a linear or branched alkyl group, it may be an alkyl group having from 1 to 8 carbon atoms; when R$_2$ is a linear or branched alkenyl group, it may be an alkenyl group having from 2 to 5 carbon atoms; when R$_2$ represents a linear or branched alkynyl group, it may be an alkynyl group having from 3 to 4 carbon atoms; when R$_2$ is a bicyclic group, it represents a norbornyl group; when R$_2$ represents an aralkyl group, it is a benzyl group; when R$_2$ represents an aryl group, it is a phenyl group optionally substituted by a halogen atom, such as, for example, a chlorine atom; when $R_2$ represents a substituted or unsubstituted cycloalkyl or cycloaliphatic alkyl group, it may contain from 3 to 6 carbon atoms; when $R_2$ represents a substituted or unsubstituted heterocyclylalkyl or heterocyclic group, it is an unsaturated five-member ring which may also contain a further heteroatom. In the above-mentioned Formula I, the amidine radical may be in the ortho, meta, or para position of the benzene ring.

Preferred compounds according to the present invention are those wherein the amidine radical is in the para position of the benzene ring and R, $R_1$, and $R_3$ are each a hydrogen atom and $R_2$ may be a hydroxyl, methyl, ethyl, n-propyl, isopropyl, n-butyl, isobutyl, sec-butyl, t-butyl, neopentyl, hexyl, heptyl, octyl, allyl, α-methylallyl, prenyl, propargyl, α-methylpropargyl, cyano, norbornyl, benzyl, cyclopropyl, cyclopropylmethyl, dimethylcyclopropylmethyl, menthyl, cyclohexyl, cyclohexylmethyl, phenyl, p-chlorophenyl, p-methylphenyl, p-methoxyphenyl, methylenedioxyphenyl, or 2-furylmethyl group, and their non-toxic acid addition salts.

The compounds of Formula I may be prepared by the following processes, which themselves constitute aspects of the invention.

Method A:

An imidazolylphenylamine of the formula

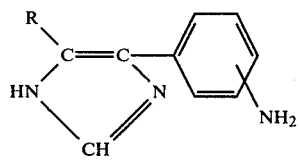 (II)

wherein R is as defined above, is reacted with a reactive derivative of a carboxamide of the formula

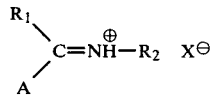 (III)

wherein $R_1$ and $R_2$ are as defined above, $X^\ominus$ represents the anion of an inorganic acid such as hydrochloride or fluoroborate, and A represents a benzoyloxy group, chlorine, or a lower alkoxy group such as methoxy or ethoxy. Optionally the compound of Formula III may be reacted as a base. The reaction is generally effected at a temperature of from about 0° to 100° C., preferably from about 20° to 60° C. The reaction is advantageously carried out in the presence of an inert organic solvent. Suitable solvents include, for example, alkanols having from 1 to 3 carbon atoms such as methanol or ethanol, halogenated hydrocarbons such as dichloromethane, dioxane, or acetone.

The compounds of Formula III used as starting material in the above process may be obtained by conventional methods by reacting a carboxamide of the formula

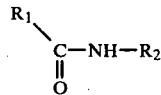 (IV)

wherein $R_1$ and $R_2$ are as defined above, with benzoylchloride, triethyloxomium fluoroborate, ethyl chloroformate, phosphorous oxychloride, or phosphorous pentachloride.

Method B:

An N-(imidazolylphenyl)imidate of the formula

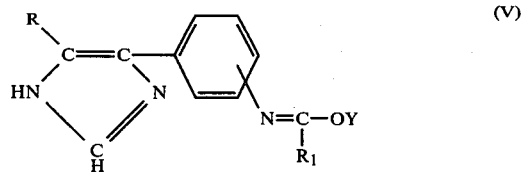 (V)

wherein R and $R_1$ are as defined above, and Y represents a lower alkyl group, such as methyl or ethyl, is reacted with an amine of the formula

$$H_2N-R_2 \qquad (VI)$$

wherein $R_2$ is as defined above.

The reaction is conveniently carried out in the presence of an inert organic solvent. Suitable solvents include, for example, alkanols such as methanol or ethanol or dioxane. The reaction may, however, be carried out in the absence of a solvent. An excess of amines of Formula VI may be used as a solvent. The reaction is generally effected at a temperature of from about 20° to 80° C.

Optionally the above reaction may effectively be carried out in a single step, by reacting amines of Formula II with a compound of the formula

 (VII)

wherein $R_1$ and Y are as defined above, in the presence of an inorganic acid, such as, for example, sulfuric acid, as catalyst. The reaction is carried out at a temperature of from about 0° to 120° C. After a few hours a suitable amine of Formula VI is added to the reaction mixture.

The compound of Formula V used as starting material can be prepared by methods known in the literature, for example, by reacting an amine of Formula II with a compound of Formula VII in the absence of solvent and distilling off the alcohol formed during the reaction.

Method C:

An N,N-disubstituted carboxamide dialkyl acetal of the formula

 (VIII)

wherein $R_1$, $R_2$, $R_3$, and Y are as defined above, is reacted with an amine of Formula II. The reaction is performed at a temperature of from about 20° to 80° C., and the alcohol formed during the reaction is distilled off.

Method D:

An N,N'-disubstituted amidine compound of the formula

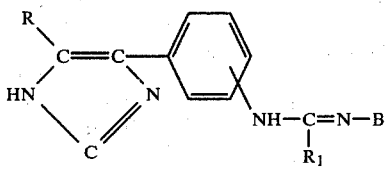

(IX)

wherein R and $R_1$ are as defined above and B represents a cyano, acetyl, carbethoxy, or carbamyl group, is reacted with amines of Formula VI.

The reaction is advantageously performed in the presence of water or of an inert organic solvent, for example, an alkanol such as methanol or ethanol, formamide, dioxane, or acetonitrile. This reaction may, for example, be effected at a temperature of from about 10° to 50° C., preperably at room temperature.

The compounds of Formula IX used as starting material in the above process are obtained by processes that are known per se in the literature, for example, by reacting an amine of Formula II with an N-substituted ethyl imidate of the formula

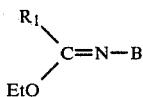

(X)

wherein $R_1$ and B are as defined above. In the alternative, when in the compound of Formula IX B represents a cyano group, the reaction may also be carried out in a single step by reacting an amine of Formula II with cyanamide in the presence of a compound of Formula VII, in which Y and $R_1$ are as defined above.

The reaction is generally carried out either in the absence of solvent or in the presence of a suitable inert organic solvent, for example, a lower alkanol, ether, ethyl acetate, acetonitrile, or dioxane, at a temperature of from about 20° to 80° C. The compound of Formula X may be prepared by conventional methods.

Method E:

An N,N'-disubstituted sulfinylamidine of the formula

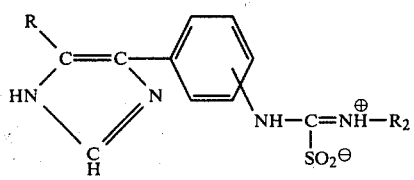

(XI)

wherein R and $R_2$ are as defined above, is reacted with a weak organic acid, for example, formic acid, acetic acid, or propionic acid.

The N,N'-disubstituted sulfinylamide of Formula XI may be obtained by conventional methods, for example, by oxidation of the corresponding thiourea by means of hydrogen peroxide in the presence of a lower alkanol at a temperature of from about 20° to 50° C.

Method F:

A 1-(N-alkyliminoformyl)-imidazole of the formula

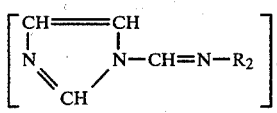

(XIII)

wherein $R_2$ is as described above, a non-isolated intermediate obtained in situ from an isonitrile of the formula

(XIIa)

and imidazole in the presence of AgCl [T. Saegusa et al., Tetrah. Letters, 1286 (1974)], is reacted with an amine of Formula II or directly by reacting an amine of Formula II with an isonitrile of Formula XIIa in the presence of CuCl. The reaction may be carried out in the absence of solvent or in the presence of an inert organic solvent, for example, ethanol or dioxane. The reaction is carried out at a temperature of from about 100° to 150° C.

The compounds of Formula I prepared according to the Methods A to F can then be converted with inorganic or organic acids into non-toxic acid addition salts as defined above, for example, by a conventional method, such as by reacting the compounds as bases with a solution of the corresponding acids in a suitable solvent. Particularly preferred acids include, for example, hydrochloric acid, maleic acid, fumaric acid, and methanesulfonic acid. The salts obtained are normally soluble in water.

As mentioned above the new compounds of general Formula I and their pharmacologically acceptable acid addition salts are $H_2$-receptor blocking agents which inhibit gastric acid secretion. Thus those compounds of Formula I wherein the amidine radical is in the para position of the benzene ring and R, $R_1$, and $R_3$ are hydrogen atoms and $R_2$ may be a hydroxyl, methyl, ethyl, n-propyl, isopropyl, n-butyl, isobutyl, sec-butyl, t-butyl, neopentyl, hexyl, heptyl, octyl, allyl, α-methylally, prenyl, propargyl, α-methylpropargyl, cyano, norbornyl, benzyl, cyclopropyl, cyclopropylmethyl, dimethylcyclopropylmethyl, menthyl, cyclohexyl, cyclohexylmethyl, phenyl, p-chlorophenyl, p-methylphenyl, p-methoxyphenyl, methylenedioxyphenyl, or 2-furylmethyl group and as well as their pharmacologically acceptable acid addition salts, generally exhibit a better activity, and therefore they are preferred as anti-ulcer agents for the treatment of disorders of the gastrointestinal tract.

Particularly preferred compounds according to the present invention include the following:

A = N-Ethyl-N'-[4-(imidazol-4-yl)-phenyl]-formamidine

B = N-Isopropyl-N'-[4-(imidazol-4-yl)-phenyl]-formamidine

C = N-Allyl-N'-[4-(imidazol-4-yl)-phenyl]-formamidine

D = N-n-Propyl-N'-[4-(imidazol-4-yl)-phenyl]-formamidine

E = N-sec-Butyl-N'-[4-(imidazol-4-yl)-phenyl]-formamidine

F = N-Isobutyl-N'-[4-(imidazol-4-yl)-phenyl]-formamidine

G = N-Prenyl-N-[4-(imidazol-4-yl)-phenyl]-formamidine

H = N-Cyclopropylmethyl-N'-[4-(imidazol-4-yl)-phenyl]-formamidine

I = N-Cyclopropyl-N'-[4-(imidazol-4-yl)-phenyl]-formamidine

J = N-(α-Methylallyl)-N'-[4-(imidazol-4-yl)-phenyl]-formamidine

K = N-Neopentyl-N'-[4-(imidazol-4-yl)-phenyl]-formamidine

L = N-(2,2-Dimethyl)-cyclopropylmethyl-N'-[4-(imidazol-4-yl)-phenyl]-formamidine The antagonistic activity on histamine $H_2$-receptors is demonstrated either in vitro or in vivo by their inhibition of the $H_2$-dependent biological effects, which include the histamine-evoked positive chronotropic effect and the histamine-induced gastric secretion of acid, respectively.

1. Determination of Histamine-evoked Chronotropic Effect

Method:

The positive chronotropic effect has been investigated in isolated guinea pig atria suspended in an organ bath (50 ml) containing oxygenated ($O_2$: 95%, $CO_2$: 5%) Krebs-Henseleit solution (pH 7.4) maintained at 32° C. The myocardial preparation, loaded at 1 gm of isometric tension, is allowed to stabilize for 60 minutes and myocardial contractions are recorded through an isometric lever connected to a strain-gauge coupler. The instantaneous rate is monitored with a cardiotachymeter and a heat-writing pen recorder. After a control run, responses (tachycardia) to histamine ($10^{-6}$ g/ml) are obtained three times at 30 minute intervals. The test compounds are added to the bath to the desired final concentration, and the atria are again injected with histamine. The chronotropic response obtained in the presence of the antagonist is then compared to the control response to histamine, and the percent reduction of the histamine $H_2$-evoked response is calculated. The average effective concentration ($EC_{50}$) of the $H_2$-antagonists is also calculated by standard repression analysis of the dose percentage response curve determined according to D. R. Waud, Analysis of Dose-response Curves, in "Methods in Pharmacology", vol. 3 Smooth Muscle, Ed Daniel E. E. Patron, M., Plenum Press. New York (1975), and Ash and Schild, Br. J. Pharmacol. Chemother. 27 427–439 (1966). The results obtained are shown in the following table:

TABLE I

| In vitro inhibitory activity in histamine-induced tachycardia (guinea pig atria) | |
|---|---|
| Compound | $EC_{50}$ ($10^{-8}$ M) |
| A | 30 |
| B | 9.2 |
| C | 9.3 |
| D | 4.4 |
| E | 15.0 |
| F | 6.5 |
| G | 7.4 |
| H | 4.8 |
| I | 37.9 |
| J | 16.8 |
| K | 12.1 |
| L | 50 |
| Cimetidine | 340.0 |

2. Determination of Histamine-induced Gastric Secretion

Some compounds of Formula I have been found to also be effective in inhibiting the spasmodic action of histamine which is inhibited by classical $H_1$-antihistamines, such as diphenydramine and pyrilamine, in the isolated guinea pig ileum. The ability of the test compounds to inhibit histamine-induced gastric secretion of acid, has been investigated after intravenous or intraduodenal administration in stomach perfused rats according to Gosh and Schild (Br. J. Pharmacol. Chemother. 13, 54 (1958).

Method:

The preparation of the animals in general anaesthesia (urethane, 1 gm/kg i.p.) and constant temperature, is achieved by inserting and typing in place polyethyl tubes (PE 50) in the esophagus and in the pyloric-antral region. After the stomach is washed to remove residual food, continuous perfusion of the stomach is started with saline, 0.5 ml/min (37° C.), primed by a Jobling peristaltic pump. After 30 minutes of perfusion adaptation, the stomach perfusate is collected in 30 minute samples, and the samples are titrated for acid content, expressed as $\mu$Eq of 1 N NaOH. As acid output becomes constant, as a control, intravenous perfusion of histamine (1 mg/kg.hr) is started and maintained throughout the experimental period. After the acid secretion has reached a steadily higher level, increasing doses of the test compounds are injected intravenously to obtain dose response functions. The $ED_{50}$ values are then calculated by standard procedure. The compounds tested by the aforementioned procedure showed a very potent anti-secretory activity when administered intravenously at or below 100 $\mu$g/kg. The results are reported in the following table:

TABLE II

| In vivo anti-secretory activity in histamine-induced gastric secretion (stomach perfused rat) | |
|---|---|
| Compound | $ED_{50}$ (mg/kg i.v.)* |
| A | 0.02 |
| B | 0.0129 |
| C | 0.024 |
| D | 0.0111 |
| E | 0.0223 |
| F | 0.0259 |
| G | 0.0559 |
| H | 0.0235 |
| I | 0.0366 |
| J | 0.042 |
| K | 0.030 |
| L | 0.034 |
| Cimetidine | 0.560 |

*The activity values are expressed with regard to the compound as a base.

3. Acute Toxicity

The acute toxicity of substances according to the invention was determined with groups of five Swiss mice, which mice had fasted for 18 hours prior to the testing. Doses of 250 mg/kg, 375 mg/kg, or 500 mg/kg were administered orally (observation time: 14 days). The results, which are expressed in terms of each compound as a base, are set forth in the following table:

TABLE III

| Compound | Acute toxicity per os |
|---|---|
| A | 500 mg/kg (3 out of 5 animals died) |
| B | 500 mg/kg (2 out of 5 animals died) |
| C | 500 mg/kg (1 out of 5 animals died) |

TABLE III-continued

| Compound | Acute toxicity per os |
|---|---|
| D | 375 mg/kg (2 out of 5 animals died) |
| E | 500 mg/kg (2 out of 5 animals died) |
| F | 250 mg/kg (2 out of 5 animals died) |
| G | 250 mg/kg (1 out of 5 animals died) |
| H | 500 mg/kg (4 out of 5 animals died) |
| I | 500 mg/kg (0 out of 5 animals died) |
| J | 500 mg/kg (2 out of 5 animals died) |
| K | 250 mg/kg (2 out of 5 animals died) |
| L | 250 mg/kg (5 out of 5 animals died) |

Due to their pharmacological properties the new compounds of Formula I are suitable for inhibiting the secretion of gastric juices in the stomach and are thus useful as anti-ulcer agents for treating ulcers in the gastrointestinal tract. For pharmaceutical purposes the compounds of the present invention are administered to warm-blooded animals perorally, parenterally, topically, or rectally as active ingredients in either liquid or solid form in customary pharmaceutical compositions, that is, compositions consisting essentially of an inert pharmaceutical carrier and an effective amount of the active ingredient, such as tablets, coated tablets, capsules, granulates, suppositories, solutions, suspensions, emulsions, ointments, gels, creams, powders, and sprays. Suitable inert pharmaceutical carriers include, for example, talc, gum arabic, lactose, gelatine, magnesium stearate, and corn starch, as well as other aqueous or non-aqueous vehicles.

Advantageously the active ingredient or a mixture of the different active ingredients of Formula I may be administered to both humans or animals, in a single dosage unit of from about 10 to 500 mg, (0.13 to 6.66 mg/kg of body weight), preferably from about 20 to 150 mg (0.27 to 2.0 mg/kg of body weight), one to three times daily. A daily dose is therefore from about 10 to 1500 mg (from about 0.13 to 20.0 mg/kg of body weight), preferably from about 20 to 450 mg (from about 0.27 to 6.0 mg/kg of body weight). Depending on the type and body weight of the patient to be treated, on the type and severity of the disease, on the type of preparation, and on the route of administration as well as on the period or interval over which the administration takes place, it may, however, be necessary to deviate from the above dosages. Thus, it may be sufficient in some cases to administer less than the above-mentioned amount of active ingredient, while in other cases the above-mentioned amount of active ingredient must be exceeded. The optimum dosage and route of administration of the active ingredients which are necessary in each case can easily be determined by one skilled in the art.

The following examples are intended to illustrate the invention and should not be construed as limiting the invention thereto.

EXAMPLES

Example 1

5-Methyl-4-(3-aminophenyl)-1-H-imidazole

Eighty-four grams of 5-methyl-4-(3-nitrophenyl)-1-H-imidazole [R. Morgenstern et al., Pharmazie 30, 103 (1975)] dissolved in methanol were hydrogenated in the presence of 0.8 gm of 5% Pd catalyst at atmospheric pressure and at room temperature. When the calculated amount of hydrogen was taken up, the catalyst was filtered off, and the remaining solution was evaporated to dryness to produce 62.5 gm of the desired compound.

M.p.: 198°–199° C.

Analysis: $C_{10}H_{11}N_3$: Calc.: C 69.34; H 6.40; N 24.26; Found: C 69.12; H 6.43; N 24.40

Example 2

5-Methyl-4-(4-aminophenyl)-1-H-imidazole (a) 5-Methyl-4-(4-nitrophenyl)-1-H-imidazole Fifty grams of 5-methyl-4-phenyl-1-H-imidazole as a nitrate salt [R. Morgenstern et al., Pharmazie 30, 103 (1975)] was added in portions to 100 ml of 96% $H_2SO_4$. The thick solution so obtained was heated at 100° C. for two hours, diluted with 1000 ml of water, and heated again to 70° C. for twenty hours. After cooling, the solution was neutralized with 30% NaOH and 17% $Na_2CO_3$ aqueous solutions. The solid precipitate (a mixture of o- and p-nitro derivatives) was removed by filtration and converted into its nitrate salt by means of 30% nitric acid. The resulting mixture of salts of the two o- and p-nitro isomers was recrystallized from water to produce pure para-isomer. Neutralization of an aqueous solution of the p-nitro derivative furnished 30 gm of 5-methyl-4-(4-nitrophenyl)-1-H-imidazole as a base sufficiently pure to be used in the next step.

M.p.: 190°–191° C.

Analysis: $C_{10}H_9N_3O_2$: Calc.: C 59.10; H 4.46; N 20.68; Found: C 58.94; H 4.42; N 20.81

(b) 5-Methyl-4-(4-aminophenyl)-1-H-imidazole

Sixty grams of 5-methyl-4-(4-nitrophenyl)-1-H-imidazole dissolved in methanol was hydrogenated in the presence of 0.7 gm of 5% Pd catalyst at atmospheric pressure and at room temperature. When the calculated amount of hydrogen was taken up, the catalyst was filtered off, and the solution was evaporated to dryness to yield 45 gm of 5-methyl-4-(4-aminophenyl)-1-H-imidazole.

M.p.: 215°–216° C.

Analysis: $C_{10}H_{11}N_3$ Calc.: C 69.34; H 6.40; N 24.26; Found: C 69.12; H 6.29; N 24.15

Example 3

(a) N-[3-(Imidazol-4-yl)-phenyl]-ethyl acetimidate

A mixture of 15.9 gm of 4-(3-aminophenyl)-1-H-imidazole [W. Schunack et al., Arch. Pharm. 306, 934 (1973)] and 18.17 gm of triethyl orthoacetate was heated until the calculated amount of ethanol was distilled. The resulting solid was recrystallized from petroleum ether/diethyl ether (1:1, v/v) to yield 21.6 gm of N-[3-(imidazol-4-yl)-phenyl]-ethyl acetimidate.

M.p.: 126°–127° C.

Analysis: $C_{13}H_{15}N_3O$: Calc.: C 68.10; H 6.59; N 18.33; Found: C 68.14; H 6.64; N 18.01

The following intermediates were prepared in similar manner:

(i) N-[3-(5-Methylimidazol-4-yl)-phenyl]-ethyl acetimidate was obtained starting from 5-methyl-4-(3-amino-phenyl)-1-H-imidazole and triethylorthoacetate.

M.p.: 130°–131° C. ($Et_2O$)

Analysis: $C_{14}H_{17}N_3O$: Calc.: C 69.11; H 7.04; N 17.27; Found: C 69.32; H 7.08; N 17.15

(ii) N-[4-(5-Methylimidazol-4-yl)-phenyl]-ethyl acetimidate was obtained starting from 5-methyl-4-(4-amino-phenyl)-1-H-imidazole and triethylorthoacetate.

M.p.: 171°–172° C. ($Et_2O$).

Analysis: $C_{14}H_{17}N_3O$: Calc.: C 69.11; H 7.04; N 17.27; Found: C 69.43; H 7.09; N 17.34

(iii) N-[4-(Imidazol-4-yl)-phenyl]-ethyl acetimidate was obtained starting from 4-(4-amino-phenyl)-1-H-imidazole [E. Balaban et al., J. Chem. Soc. 2701 (1925)] and triethylorthoacetate.

M.p.: 144°–147° C. (Et$_2$O).

Analysis: $C_{13}H_{15}N_3O$: Calc.: C 68.10; H 6.59; N 18.33; Found: C 68.21; H 6.60; N 18.14

(b)

N-Methyl-N'-[4-(imidazol-4-yl)-phenyl]-acetamidine

Three portions of 8 gm of 33% methylamine in ethanol were added over a period of six days to a solution of 8.02 gm of N-[4-(imidazol-4-yl)-phenyl]-ethyl acetimidate in 20 ml of ethanol. The resulting solution was evaporated to dryness, and the residue was dissolved in 10% hydrochloric acid. The acid solution was washed with ethyl acetate and adjusted to pH 10 with 10% NaOH. The solid which precipitated was collected by filtration and dried to yield 5.5 gm of the desired compound.

M.p.: 226°–227° C.

Analysis: $C_{12}H_{14}N_4$: Calc.: C 67.26; H 6.59; N 26.15; Found: C 67.53; H 6.53; N 25.98

The maleate salt was prepared by reaction with maleic acid. The melting point of the salt was 170°–171° C.

The following acetamidines were prepared in similar manner, starting from the appropriate ethyl acetimidate as described above.
(i) N-Methyl-N'-[3-(5-methylimidazol-4-yl)-phenyl]-acetamidine M.p.: 201°–202° C.

Analysis: $C_{13}H_{16}N_4$: Calc.: C 68.39; H 7.06; N 24.54; Found: C 67.77; H 7.05; N 24.18

Hydrochloride salt. M.p.: 260°–261° C.
(ii) N-Methyl-N'-[3-(imidazol-4-yl)-phenyl]-acetamidine M.p. 117°–120° C.

Analysis: $C_{12}H_{14}N_4$: Calc.: C 67.26; H 6.59; N 26.15; Found: C 66.86; H 6.81; N 25.82

Hydrochloride salt. M.p.: 288°–290° C.
(iii) N-Methyl-N'-[4-(5-Methylimidazol-4-yl)-phenyl]-acetamidine M.p.: 223°–226° C.

Analysis: $C_{13}H_{16}N_4$: Calc.: C 68.39; H 7.06; N 24.54; Found: C 68.45; H 7.08; N 24.36

Hydrochloride salt. M.p.: 283°–285° C.

EXAMPLE 4

N-Methyl-N'-[4-(imidazol-4-yl)-phenyl]-formamidine

A solution of 5.62 gm of benzoyl chloride in 30 ml of anhydrous diethyl ether was added to a solution of 2.36 gm of N-methylformamide in 10 ml of anhydrous diethyl ether. After one hour of stirring, the white solid which formed was collected by filtration and immediately added to a suspension of 1.59 gm 4-(4-aminophenyl)-1-H-imidazole in 50 ml of dioxane. The mixture was stirred overnight and then evaporated to dryness. The residue was taken up in water, the solution was adjusted to pH 10 with 10% NaOH, and the product which separated was extracted with ethyl acetate. The organic solution was dried (MgSO$_4$) and evaporated to dryness to give 0.75 gm of the crude amidine, which was recrystallized from acetone.

M.p.: 189°–190° C.

Analysis: $C_{11}H_{12}N_4$: Calc.: C 65.98; H 6.04; N 27.98; Found: C 65.55; H 5.92; N 27.56

Fumarate salt. M.p.: 188°–189° C.

EXAMPLE 5

N-Methyl-N'-[4-(imidazol)-4-yl)-phenyl]-formamidine

To a solution of 1.48 gm of N-methylformamide in 15 ml of dichloromethane, a solution of 4.78 gm of triethyloxonium fluoroborate [H. Meerwein, Org. Synth. 46, 113 (1966)] in 25 ml of dichloromethane was added slowly at 0° C. After six hours of stirring at room temperature, 2 gm of 4-(4-aminophenyl)-1-H-imidazole in 10 ml of ethanol was added dropwise. The mixture was stirred overnight and then evaporated to dryness. The fluoroborate salt of N-methyl-N'-[4-(imidazol-4-yl)-phenyl]-formamidine was dissolved in water, and the solution was adjusted to pH 10 with 10% NaOH. The product which crystallized was collected by filtration to give 1.4 gm of the desired compound.

M.p.: 189°–190° C.

The following compounds were prepared in similar manner, starting from the appropriate imidazolyl-phenylamine and from the suitable N-substituted formamide:
(i) N-tert-Butyl-N'-[4-(imidazol-4-yl)-phenyl]-formamidine Fumarate salt. M.p.: 192°–194° C. (ethanol).

Analysis: $C_{22}H_{26}N_4O_8$: Calc.: C 55.69; H 5.52; N 11.81; Found: C 55.94; H 5.67; N 11.68
(ii) N-Menthyl-N'-[4-(imidazol-4-yl)-phenyl]-formamidine Tartrate salt. M.p.: 106°–109° C.

Analysis: $C_{28}H_{40}N_4O_{12}$: Calc.: C 53.84; H 6.45; N 8.97; Found: C 53.99; H 6.48; N 8.94

EXAMPLE 6

(a)

N-Methyl-N'-[4-(imidazol-4-yl)-phenyl]-formamidine

A suspension of 0.8 gm of 4-(4-aminophenyl)-1-H-imidazole and 1.86 gm of ethyl N-methyl-formimidate hydrochloride [F. H. Suydam et al., J. Org. Chem. 34, 292 (1969)] in 20 ml of anhydrous ethanol was stirred at room temperature for two days. The clear solution was evaporated to dryness, and the oily residue was dissolved in water. The solution so obtained was adjusted to pH 10 with 10% NaOH. The product which separated was extracted with ethyl acetate, the organic solution was evaporated to dryness, and the product obtained was purified through its hydorchloride salt to give 0.35 gm of the desired compound as crystalline solid.

M.p.: 280°–282° C. (ethanol).

Analysis: $C_{11}H_{14}Cl_2N_4$: Calc.: C 48.36; H 5.17; Cl 25.96; N 20.51; Found: C 47.98; H 5.26; Cl 25.78; N 20.21

(b)

N-Phenyl-N'-[4-(imidazol-4-yl)-phenyl]-formamidine

Five grams of 4-(4-aminophenyl)-1-H-imidazole were added to a solution of 4.6 gm of ethyl N-phenyl-formimidate [Org. Synth., 35, 65 (1965)] in 25 ml of acetone. After stirring for four hours at room temperature, the solid that separated was filtered and dried under vacuum. The product was treated with acetone and acidified with glacial acetic acid. N-Phenyl-N'-[4-(imidazol-4-yl]-formamidine crystallized as acetate salt which was filtered to give 4.6 gm of the desired product.

M.p.: 123°–124° C.

Analysis: $C_{20}H_{22}N_4O_4$: Calc.: C 62.81; H 5.80; N 14.65; Found: C 62.58; H 5.72; N 14.69

The following compounds were prepared in similar manner, starting from the appropriate imidazolyl-phenylamine and from the suitable ethyl formimidates:
(i) N-3,4-Methylenedioxyphenyl-N'-[4-(imidazol-4-yl)-phenyl]-formamidine
Fumarate salt. M.p.: 140°–141° C.
Analysis: $C_{25}H_{22}N_4O_{10}$: Calc.: C 55.76; H 4.12; N 10.41; Found: C 55.48; H 4.15; N 10.50
(ii) N-4-Chlorophenyl-N'-[4-(imidazol-4-yl)-phenyl]-formamidine
Acetate salt. M.p.: 78°–79° C.
Analysis: $C_{20}H_{21}ClN_4O_4$: Calc.: C 57.62; H 5.08; Cl 8.50; N 13.44; Found: C 57.73; H 5.12; Cl 8.63; N 13.36
(iii) N-4-Tolyl-N'-[4-(imidazol-4-yl)-phenyl]-formamidine
Acetate salt. M.p.: 91°–92° C.
Analysis: $C_{21}H_{24}N_4O_4$: Calc.: C 63.62; H 6.10; N 14.13; Found: C 62.98; H 6.13; N 14.08
(iv) N-4-Anisyl-N'-[4-(imidazol-4-yl)-phenyl]-formamidine
Fumarate salt. M.p.: 131°–132° C.
Analysis: $C_{25}H_{24}N_4O_9$: Calc.: C 57.25; H 4.61; N 10.68; Found: C 57.01; H 4.64; N 10.71
(v) N-(3,4-Dimethylisoxazol-5-yl)-N'-[4-(imidazol-4-yl)-phenyl]-formamidine
M.p.: 204°–205° C.
Analysis: $C_{15}H_{15}N_5O$: Calc.: C 64.04; H 5.37; N 24.90; Found: C 63.91; H 5.40; N 24.85

EXAMPLE 7

(a)

N-Cyano-N'-[4-(imidazol-4-yl)-phenyl]-formamidine

A solution of 25.3 gm of 4-(4-aminophenyl-1-H-imidazole and 18.7 gm of ethyl N-cyano-formimidate [K. R. Huffman et al., J. Org. Chem. 28, 1816 (1963)] in ethanol was stirred at room temperature overnight. The product, which crystallized at the end of the reaction, was collected by filtration and washed with cold ethanol to yield 30.7 gm of the desired compound.
M.p.: 234°–235° C.
Analysis: $C_{11}H_9N_5$: Calc.: C 62.55; H 4.30; N 33.16; Found: C 61.94; H 4.36; N 32.95

The following compounds were prepared in similar manner, starting from the appropriate imidazolyl phenyl amine:
(i) N-Cyano-N'-[3-(imidazol-4-yl)-phenyl]-formamidine
M.p.: 206°–207° C.
Analysis: $C_{11}H_9N_5$: Calc.: C 62.55; H 4.30; N 33.16; Found: C 62.60; H 4.22; N 32.84
(ii) N-Cyano-N'-[4-(5-methylimidazol-4-yl)-phenyl]-formamidine
M.p.: 236°–238° C.
Analysis: $C_{12}H_{11}N_5$: Calc.: C 63.98; H 4.92; N 31.09; Found: C 63.44; H 5.04; N 30.94
(iii) N-Cyano-N'-[3-(5-methylimidazol-4-yl)-phenyl]-formamidine
M.p.: 221°–223° C.
Analysis: $C_{12}H_{11}N_5$: Calc.: C 63.98; H 4.92; N 31.09; Found: C 63.96; H 5.06; N 30.82

(a')

N-Cyano-N'-[4-(imidazol-4-yl)-phenyl]-formamidine

A mixture of 113.8 gm of 4-(p-aminophenyl)-1-H-imidazole, 132.4 gm of ethyl orthoformate, and 30.7 gm of cyanamide was heated at 100° C. for 20 minutes and then stirred at room temperature for three hours. The solid that formed was collected by filtration and dried to give 130 gm of the desired compound.
M.p.: 236°–238° C.

(b)

N-Methyl-N'-[4-(imidazol-4-yl)-phenyl]-formamidine

Twenty grams of N-cyano-N'-[4-(imidazol-4-yl)-phenyl]-formamidine was added in one portion to 35% methylamine in water (70 ml). A few minutes after the addition, the solid N-methyl-N'-[4-(imidazol-4-yl)-phenyl]-formamidine separated out of the solution. This solid was collected by filtration, washed with water, and dried to yield 13.45 gm of the desired product, which was recrystallized from acetone.
M.p.: 189°–190° C.
Fumarate salt. M.p.: 188°–189° C.

The following compounds were prepared in similar manner, starting from the appropriate N-cyano-formamidine derivatives.
(i) N-Methyl-N'-[3-(imidazol-4-yl)-phenyl]-formamidine
Maleate salt. M.p.: 149°–150° C. (ethanol).
Analysis: $C_{19}H_{20}N_4O_8$: Calc.: C 52.78; H 4.66; N 12.96; Found: C 51.93; H 4.73; N 13.15
(ii) N-Methyl-N'-[3-(5-methylimidazol-4-yl)-phenyl]-formamidine
M.p.: 180°–181° C.
Analysis: $C_{12}H_{14}N_4$: Calc.: C 67.26; H 6.59; N 26.15; Found: C 67.40; H 6.67; N 26.40
(iii) N-Methyl-N'-[4-(5-methylimidazol-4-yl)-phenyl]-formamidine
M.p.: 225°–226° C.
Analysis: $C_{12}H_{14}N_4$: Calc.: C 67.26; H 6.59; N 26.15; Found: C 66.81; H 6.70; N 25.82
(iv) N-Ethyl-N'-[4-(imidazol-4-yl)-phenyl]-formamidine
Hydrochloride salt. M.p.: 253°–254° C.
Analysis: $C_{12}H_{16}Cl_2N_4$: Calc.: C 50.18; H 5.61; Cl 24.69; N 19.51; Found: C 49.92; H 5.70; Cl 25.00; N 19.56
(v) N-Butyl-N'-[4-(imidazol-4-yl)-phenyl]-formamidine
Hydrochloride salt. M.p.: 206°–208° C.
Analysis: $C_{14}H_{20}Cl_2N_4$: Calc.: C 53.34; H 6.39; Cl 22.49; N 17.77; Found: C 53.48; H 6.51; Cl 22.63; N 17.59
(vi) N-Isopropyl-N'-[4-(imidazol-4-yl)-phenyl]-formamidine
Fumarate salt. M.p.: 130°–133° C.
Analysis: $C_{21}H_{24}N_4O_8$: Calc.: C 54.78; H 5.25; N 12.17; Found: C 53.91; H 5.30; N 12.36
(vii) N-Allyl-N'-[4-(imidazol-4-yl)-phenyl]-formamidine
Maleate salt. M.p.: 153°–154° C.
Analysis: $C_{21}H_{22}N_4O_8$: Calc. C 55.02; H 4.84; N 12.22; Found: C 54.85; H 4.71; N 11.93
(viii) N-Hydroxy-N'-[4-(imidazol-4-yl)-phenyl]-formamidine
Hydrochloride salt. M.p.: 207°–208° C.
Analysis: $C_{10}H_{12}Cl_2N_4O$: Calc.: C 43.65; H 4.39; Cl 25.76; N 20.36; Found: C 43.70; H 4.34; Cl 25.48; N 20.45
(ix) N-n-Propyl-N'-[4-(imidazol-4-yl)-phenyl]-formamidine
Hydrochloride salt. M.p.: 220°–221° C. (ethanol).
Analysis: $C_{13}H_{18}Cl_2N_2$: Calc.: C 51.83; H 6.02; Cl 23.54; N 18.60; Found: C 51.13; H 6.10; Cl 23.30; N 18.51

(x) N-sec-Butyl-N'-[4-(imidazol-4-yl)-phenyl]-formamidine
Hydrochloride salt. M.p.: 196°–197° C. (ethanol).
Analysis: $C_{14}H_{20}Cl_2N_4$: Calc.: C 53.33; H 6.39; Cl 22.49; N 17.77; Found: C 52.97; H 6.51; Cl 22.08; N 17.44

(xi) N-Isobutyl-N'-[4-(imidazol-4-yl)-phenyl]-formamidine
Hydrochloride salt. M.p.: 238°–240° C. (ethanol).
Analysis: $C_{14}H_{20}Cl_2N_4$: Calc.: C 53.33; H 6.39; Cl 22.49; N 17.77; Found: C 52.69; H 6.54; Cl 22.04; N 17.38

(xii) N-(1-Methyl)-n-hexyl-N'-[4-(imidazol-4-yl)-phenyl]-formamidine
Maleate salt. M.p.: 150°–151° C. (acetone)
Analysis: $C_{25}H_{32}N_4O_8$: Calc.: C 58.13; H 6.24; N 10.85; Found: C 59.09; H 6.08; N 10.63

(xiii) N-Prenyl-N'-[4-(imidazol-4-yl)-phenyl]-formamidine
Fumarate salt. M.p.: 174°–175° C. (ethanol).
Analysis: $C_{23}H_{26}N_4O_8$: Calc.: C 56.78; H 5.39; N 11.52; Found: C 56.94; H 5.48; N 11.67

(xiv) N-Propargyl-N'-[4-(imidazol-4-yl)-phenyl]-formamidine
Methanesulfonate salt. M.p.: 184°–185° C. (ethanol).
Analysis: $C_{15}H_{20}N_4O_6S_2$: Calc.: C 43.26; H 4.84; N 13.45; S 15.39; Found: C 42.75; H 4.93; N 13.20; S 15.29

(xv) N-n-Hexyl-N'-[4-(imidazol-4-yl)-phenyl]-formamidine
Hydrochloride salt. M.p.: >270° C. (ethanol).
Analysis: $C_{16}H_{24}Cl_2N_4$: Calc.: C 55.97; N 7.05; Cl 20.66; N 16.32; Found: C 55.35; N 7.00; Cl 20.39; N 16.00

(xvi) N-Cyclopropylmethyl-N'-[4-(imidazol-4-yl)-phenyl]-formamidine
Fumarate salt. M.p.: 127°–128° C.
Analysis: $C_{22}H_{24}N_4O_8$: Calc.: C 55.93; H 5.12; N 11.86; Found: C 56.21; H 5.09; N 11.99

(xvii) N-Bicyclo-[2.2.1]-hept-2-yl-N'-[4-(imidazol-4-yl)-phenyl]-formamidine
Maleate salt. M.p.: 182°–183° C.
Analysis: $C_{25}H_{28}N_4O_8$: Calc.: C 58.58; H 5.51; N 10.93; Found: C 57.90; H 5.43; N 10.94

(xviii) N-Furfuryl-N'-[4-(imidazol-4-yl)-phenyl]-formamidine
Hydrochloride salt. M.p.: 215°–217° C. (ethanol).
Analysis: $C_{15}H_{16}Cl_2N_4O$: Calc.: C 53.11; H 4.75; Cl 20.90; N 16.52; Found: C 52.80; H 4.87; Cl 20.62; N 16.27

(xix) N-Cyclohexyl-N'-[4-(imidazol-4-yl)-phenyl]-formamidine
Fumarate salt. M.p.: 139°–141° C. (ethanol).
Analysis: $C_{24}H_{28}N_4O_8$: Calc.: C 57.59; H 5.64; N 11.20; Found: C 57.89; H 5.68; N 10.99

(xx) N-Benzyl-N'-[4-(imidazol-4-yl)-phenyl]-formamidine
Hydrochloride salt. M.p.: 210°–212° C. (ethanol).
Analysis: $C_{17}H_{18}Cl_2N_4$: Calc.: C 58.46; H 5.19; Cl 20.30; N 16.04; Found: C 57.91; H 5.29; Cl 19.94; N 15.87

(xxi) N-Cyclopropyl-N'-[4-(imidazol-4-yl)-phenyl]-formamidine
Fumarate salt. M.p.: 185°–186° C. (ethanol).
Analysis: $C_{21}H_{22}N_4O_8$: Calc.: C 55.02; H 4.84; N 12.22; Found: C 55.09; H 4.74; N 12.48

(xxii) N-(α-Methylpropargyl)-N'-[4-(imidazol-4-yl)-phenyl]-formamidine
Maleate salt. M.p.: 188° C.
Analysis: $C_{22}H_{22}N_4O_8$: Calc.: C 56.16; H 4.17; N 11.91; Found: C 56.28; H 4.15; N 11.87

(xxiii) N-(α-Methylallyl)-N-[4-(imidazol-4-yl)-phenyl]-formamidine
Maleate salt. M.p.: 186° C.
Analysis: $C_{22}H_{24}N_4O_8$: Calc.: C 55.93; H 5.12; N 11.86; Found: C 55.87; H 5.04; N 11.76

(xxiv) N-n-Octyl-N'-[4-(imidazol-4-yl)-phenyl]-formamidine
Fumarate salt. M.p.: 152°–153° C.
Analysis: $C_{26}H_{34}N_4O_8$: Calc.: C 58.85; H 6.46; N 10.56; Found: C 58.52; H 6.35; N 10.72

(xxv) N-Neopentyl-N'-[4-(imidazol-4-yl)-phenyl]-formamidine
Fumarate salt. M.p.: 251°–252° C.
Analysis: $C_{23}H_{28}N_4O_8$: Calc.: C 56.55; H 5.78; N 11.47; Found: C 56.67; H 5.81; N 11.40

(xxvi) N-(2,2-Dimethyl)-cyclopropylmethyl-N'-[4-(imidazol-4-yl)-phenyl]-formamidine
Hydrochloride salt. M.p.: 246°–248° C.
Analysis: $C_{16}H_{22}Cl_2N_4$: Calc.: C 56.30; H 6.50; Cl 20.78; N 16.42; Found: C 55.90; H 6.53; Cl 20.88; N 16.30

(xxvii) N-Cyclohexylmethyl-N'-[4-(imidazol-4-yl)-phenyl]-formamidine
Fumarate salt. M.p.: 154°–155° C.
Analysis: $C_{25}H_{30}N_4O_8$: Calc.: C 58.36; H 5.88; N 10.89; Found: C 57.79; H 5.91; N 10.75

EXAMPLE 8

N,N-Dimethyl-N'-[4-(imidazol-4-yl)-phenyl]-formamidine

A solution of 3.18 gm of 4-(4-aminophenyl)-1-H-imidazole in 8.82 gm of N,N-dimethyl-formamide diethyl acetal was stirred at room temperature for two days. Addition of diethyl ether resulted in precipitation of the formamidine, which was collected by filtration.
Yield: 3.9 gm,
M.p.: 141°–142° C.
Analysis: $C_{12}H_{14}N_4$: Calc.: C 67.26; H 6.59; N 26.15; Found: C 67.02; H 6.50; N 26.28

Example 9

N,N-Dimethyl-N'-[4-(5-methylimidazol-4-yl)-phenyl]-formamidine

The above compound was prepared from 5-methyl-4-(4-aminophenyl)-1-H-imidazole using a procedure analogous to that of Example 8.
M.p.: 228°–229° C.
Analysis: $C_{13}H_{16}N_4$: Calc.: C 68.39; H 7.06; N 24.54; Found: C 69.08; H 7.16; N 24.28

Example 10

N-Methyl-N'-[4-(imidazol-4-yl)-phenyl]-formamidine

A mixture of 1.59 gm of 4-(4-aminophenyl)-1-H-imidazole and 2.22 gm of triethylorthoformate was heated for 30 minutes at 100° C. in the presence of a catalytic amount of 96% $H_2SO_4$. A 33% solution of methylamine in ethanol (9.5 gm) was then added dropwise to the cooled reaction mixture. The solution was stirred at room temperature for twenty hours and then evaporated to dryness. The residue obtained was dissolved in 10% hydrochloric acid, and the acid solution was washed with ethyl acetate and then adjusted to pH 10 with 10% NaOH. The product which separated was extracted with ethyl acetate to yield, after evaporation of the solvent, 0.45 gm of the desired compound.

M.p.: 188°–189° C.

Example 11

(a) N-Methyl-N'-[4-(imidazol-4-yl)-phenyl]-thiourea

A solution of 2.3 gm of 4-(4-aminophenyl)-1-H-imidazole and 1.15 gm of methyl isothiocyanate in 30 ml of ethanol was refluxed for thirty minutes and evaporated to dryness. The oily base so obtained was purified by conversion into the corresponding hydrochloride salt by bubbling gaseous hydrochloric acid in isopropanol. The desired thiourea was obtained as a white solid.

Yield: 2 gm,

M.p.: 210°–211° C.

Analysis: $C_{11}H_{13}ClN_4S$: Calc.: C 49.15; H 4.87; Cl 13.19; N 20.84; S 11.92; Found: C 49.23; H 4.98; Cl 13.20; N 20.64; S 11.72

(b) N-Methyl-N'-[4-(imidazol-4-yl)-phenyl]-formamidine sulfinic acid

Hydrogen peroxide (31%, 1.08 gm) was added dropwise over a period of thirty minutes to a stirred, ice-cooled solution of 1.16 gm of N-methyl-N'-[4-(imidazol-4-yl)-phenyl]-thiourea in 5 ml of methanol. After two hours of stirring, the mixture was evaporated to dryness, and the residue so obtained was crystallized from ethanol to yield 0.95 gm of the desired compound.

Analysis: $C_{11}H_{12}N_4O_2S$: Calc.: C 49.98; H 4.57; N 21.20; S 12.12; Found: C 50.17; H 4.55; N 21.41; S 12.04

Acetate salt. M.p.: 194°–195° C. (acetone).

(c) N-Methyl-N'-[4-(imidazol-4-yl)-phenyl]-formamidine

An amount of 0.9 gm of N-methyl-N'-[4-(imidazol-4-yl)-phenyl]-formamidine sulfinic acid was dissolved in 15 ml of glacial acetic acid and refluxed for one hour. The concentrated solution was adjusted to pH 10 with 10% NaOH and extracted with ethyl acetate. The organic solution was evaporated to dryness to yield 0.3 gm of N-methyl-N'-[4-(imidazol-4-yl)-phenyl]-formamidine. M.p.: 187°–189° C.

Example 12

N-t.Butyl-N'-[4-(imidazol-4-yl)-phenyl]-formamidine

A mixture of 2.3 gm of 4-(p-aminophenyl)-1-H-imidazole, 1.25 gm of t-butylisonitrile, 0.2 gm of AgCl, and 0.11 gm of imidazole was heated at 100° C. for 13 hours. The thick reaction mixture was treated with 10% HCl and ethyl acetate. The acid solution was adjusted to pH 6.5 with 10% NaOH, treated with charcoal, filtered, and adjusted to an alkaline pH. The layer which separated was extracted with ethyl acetate. After drying, the organic solution was evaporated to dryness to yield 0.38 gm of the desired compound.

Fumarate salt. M.p.: 192°–194° C.

EXAMPLE 13

N-Cyclohexyl-N'-[4-(imidazol-4-yl)-phenyl]-formamidine

A mixture of 1.59 gm of 4-(p-aminophenyl)-1-H-imidazole, 1.2 gm of cyclohexyl isonitrile, and 0.99 gm of CuCl was heated at 150° C. for three hours. The thick reaction mixture was extracted with methanol. The methanol solution, after treatment with charcoal, was evaporated to dryness and extracted with ethyl acetate and 10% hydrochloric acid. The acid solution was adjusted to pH 7.5 with 17% $Na_2CO_3$ and extracted with ethyl acetate. The organic solution was evaporated to dryness. The substance remaining after recrystallization from acetone comprised 0.25 gm of the desired product.

M.p.: 220°–221° C.

Fumarate salt. M.p.: 139°–141° C.

The following examples illustrate a few pharmaceutical dosage unit compositions comprising a compound of the invention as active ingredient.

Example 14

Tablets Containing 50.0 mg of Active Ingredient

Each tablet was compounded from the following ingredients:

| Component | Amount (mg) |
| --- | --- |
| Active ingredient | 50.0 |
| Lactose | 217.0 |
| Corn starch | 30.0 |
| Magnesium stearate | 3.0 |
| TOTAL: | 300.0 |

Preparation:

The active ingredient, lactose, and corn starch were mixed and homogeneously moistened with water. After screening of the moist mass (mesh size 2.0 mm) and drying at 50° C. in a tray drier, the mixture was again passed through a screen (mesh size 1.5 mm) and the magnesium stearate lubricant was added. Then the mixture was pressed into tablets.

| | | |
| --- | --- | --- |
| Weight of tablet: | 300 mg | |
| Diameter: | 10 mm, | biplanar with a facet on both sides and a notch on one side. |

Example 15

Gelatine Capsules Containing 50.0 mg of Active Ingredient

Each capsule contained a mixture having the following composition:

| Component | Amount (mg) |
| --- | --- |
| Active ingredient | 50.0 |
| Corn starch, dried | 170.0 |
| Magnesium stearate | 2.0 |
| TOTAL: | 222.0 |

Preparation:

The active ingredient was mixed with the auxiliary products, and the mixture was passed through a screen of mesh size 0.75 mm and mixed homogeneously in a suitable device. The resulting mixture was filled into hard gelatine capsules of size 1.

| | |
| --- | --- |
| Content of capsule: | 222.0 mg |
| Capsule: | hard gelatine capsule size 1. |

Example 16

Vials Containing 50.0 gm of Active Ingredient

Each vial contained a solution having the following composition:

| Component | Amount |
| --- | --- |
| Active ingredient | 50.0 gm |
| Distilled water q.s. ad | 5 ml |

Preparation:

The active ingredient was dissolved in the water in appropriate amounts, and then the resulting solution was introduced into 5 ml vials under sterile conditions.

Any one of the compounds embraced by Formula I, or a combination thereof, may be used as the active ingredient employed in Examples 14 through 16. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

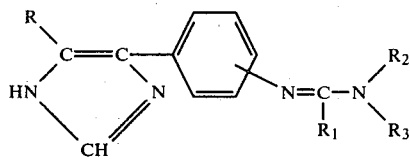

in which R, $R_1$, and $R_3$, which may be the same or different, each represent a hydrogen atom or a lower alkyl group, and $R_2$ represents a linear or branched alkyl, alkenyl, or alkynyl group, a cyano group, a hydroxyl group, a substituted or unsubstituted cycloalkyl or cycloaliphatic alkynyl group, a bicyclic group, an aralkyl or aryl group optionally substituted by halogen, methyl, methoxy, or methylenedioxy groups, or a substituted or unsubstituted heterocyclicalkyl or heterocyclic group which may also contain a further hetero atom, or a non-toxic, pharmacologically acceptable acid addition salt thereof.

2. A compound of claim 1, wherein the acid addition salt is formed with hydrochloric acid, fumaric acid, methanesulfonic acid, or maleic acid.

3. A compound of claim 1, wherein R, $R_1$, and $R_3$ each represent a hydrogen atom.

4. A compound of claim 1 or 3, wherein the amidine radical is in the para position of the benzene ring.

5. A compound of claim 1, wherein $R_2$ represents a hydroxyl, methyl, ethyl, n-propyl, isopropyl, n-butyl, isobutyl, sec-butyl, t-butyl, neopentyl, hexyl, heptyl, octyl, allyl, α-methylallyl, prenyl, propargyl, α-methylpropargyl, cyano, norbornyl, benzyl, cyclopropyl, cyclopropylmethyl, dimethylcyclopropylmethyl, menthyl, cyclohexyl, cyclohexylmethyl, phenyl, p-chlorophenyl, p-methylphenyl, p-methoxyphenyl, methylenedioxyphenyl, or 2-furylmethyl group.

6. The compound of claim 1 which is N-ethyl-N'-[4-(imidazol-4-yl)-phenyl]-formamidine or a non-toxic, pharmacologically acceptable acid addition salt thereof.

7. The compound of claim 1 which is N-isopropyl-N'-[4-(imidazol-4-yl)-phenyl]-formamidine or a non-toxic, pharmacologically acceptable acid addition salt thereof.

8. The compound of claim 1 which is N-allyl-N'-[4-(imidazol-4-yl)-phenyl]-formamidine or a non-toxic, pharmacologically acceptable acid addition salt thereof.

9. The compound of claim 1 which is N-n-propyl-N'-[4-(imidazol-4-yl)-phenyl]-formamidine or a non-toxic, pharmacologically acceptable acid addition salt thereof.

10. The compound of claim 1 which is N-sec-butyl-N'-[4-(imidazol-4-yl)-phenyl]-formamidine or a non-toxic, pharmacologically acceptable acid addition salt thereof.

11. The compound of claim 1 which is N-isobutyl-N'-[4-(imidazol-4-yl)-phenyl]-formamidine or a non-toxic, pharmacologically acceptable acid addition salt thereof.

12. The compound of claim 1 which is N-prenyl-N'-[4-(imidazol-4-yl)-phenyl]-formamidine or a non-toxic, pharmacologically acceptable acid addition salt thereof.

13. The compound of claim 1 which is N-cyclopropylmethyl-N'-[4-(imidazol-4-yl)-phenyl]-formamidine or a non-toxic, pharmacologically acceptable acid addition salt thereof.

14. The compound of claim 1 which is N-cyclopropyl-N'-[4-(imidazol-4-yl)-phenyl]-formamidine or a non-toxic, pharmacologically acceptable acid addition salt thereof.

15. The compound of claim 1 which is N-(α-methylallyl)-N'-[4-(imidazol-4-yl)-phenyl]-formamidine or a non-toxic, pharmacologically acceptable acid addition salt thereof.

16. The compound of claim 1 which is N-neopentyl-N'-[4-(imidazol-4-yl)-phenyl]-formamidine or a non-toxic, pharmacologically acceptable acid addition salt thereof.

17. The compound of claim 1 which is N-(2,2-dimethyl)cyclopropylmethyl-N'-[4-(imidazol-4-yl)-phenyl]-formamidine or a non-toxic, pharmacologically acceptable acid addition salt thereof.

18. A pharmaceutical composition for the treatment of disorders of the gastrointestinal tract which consists essentially of inert, pharmacologically acceptable carrier and an effective amount of a compound of claim 1.

19. A method for the treatment of disorders of the gastrointestinal tract which comprises perorally, parenterally, rectally, or topically administering to a warm-blooded animal or person in need of such treatment an effective amount of a compound of claim 1.

20. The method of claim 19 which is a method for treating ulcers.

* * * * *

UNITED STATES PATENT AND TRADEMARK OFFICE
CERTIFICATE OF CORRECTION

PATENT NO. : 4,386,099    Page 1 of 2

DATED : May 31, 1983

INVENTOR(S) : Enzo Cereda et al.

It is certified that error appears in the above-identified patent and that said Letters Patent are hereby corrected as shown below:

Column 2, line 6, "(1981)" should read --681(1978)--.

Column 5, lines 5 to 12, the Formula IX should read:

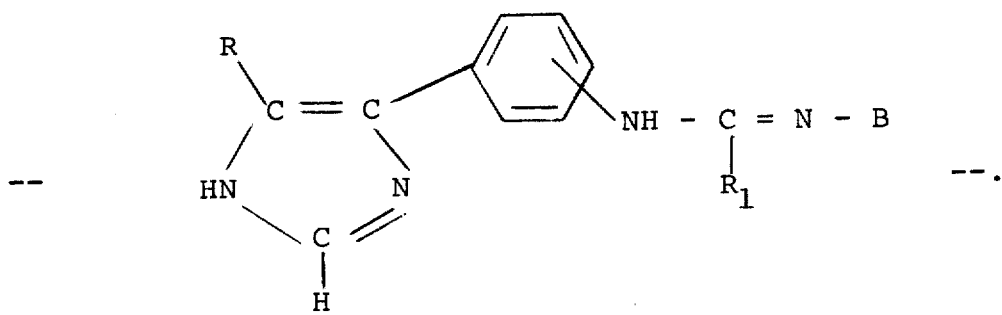

Column 6, line 18, "1286" should read --1283--.

Column 7, line 44, "repression" should read --regression--.

Column 12, line 60, "(1965)" should read --(1955)--.

UNITED STATES PATENT AND TRADEMARK OFFICE
CERTIFICATE OF CORRECTION

PATENT NO. : 4,386,099

DATED : May 31, 1983

INVENTOR(S) : Enzo Cereda et al.

It is certified that error appears in the above-identified patent and that said Letters Patent is hereby corrected as shown below:

Column 19, line 42, i.e., line 8 of Claim 1, "alkynyl" should read --alkyl--.

*Signed and Sealed this*

*Twenty-first* Day of *February 1984*

[SEAL]

*Attest:*

GERALD J. MOSSINGHOFF

*Attesting Officer*  *Commissioner of Patents and Trademarks*